(12) United States Patent
Brimhall (10) Patent No.: US 6,224,569 B1
(45) Date of Patent: *May 1, 2001

(54) COMPACT NEEDLE POINT SHIELD

(75) Inventor: Greg L. Brimhall, West Jordan, UT (US)

(73) Assignee: Becton, Dickinson and Company, Franklin Lakes, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/405,203

(22) Filed: Sep. 24, 1999

(51) Int. Cl.[7] .................................................. A61M 5/178
(52) U.S. Cl. .......................... 604/164; 604/198; 604/264
(58) Field of Search ................................. 604/164, 158, 604/165, 192, 198, 263, 264

(56) References Cited

U.S. PATENT DOCUMENTS

| Re. 34,416 | 10/1993 | Lemieux | 604/164 |
|---|---|---|---|
| 4,810,248 | 3/1989 | Masters et al. | 604/192 |
| 4,816,024 | 3/1989 | Sitar et al. | 604/192 |
| 4,832,696 | 5/1989 | Luther et al. | 604/164 |
| 4,846,811 | 7/1989 | Vanderhoof | 604/263 |
| 4,964,854 | 10/1990 | Luther | 604/166 |
| 4,978,344 | 12/1990 | Dombrowski et al. | 604/198 |
| 4,994,041 | 2/1991 | Dombrowski et al. | 604/164 |
| 5,085,648 | 2/1992 | Purdy et al. | 604/198 |
| 5,135,504 | 8/1992 | McLees | 604/164 |
| 5,215,528 | 6/1993 | Purdy et al. | 604/164 |
| 5,300,045 | 4/1994 | Plassche, Jr. | 604/263 |
| 5,409,461 | 4/1995 | Steinman | 604/110 |
| 5,558,651 | 9/1996 | Crawford et al. | 604/263 |
| 5,601,536 | 2/1997 | Crawford et al. | 604/263 |
| 5,613,952 | 3/1997 | Pressly, Sr. et al. | 604/110 |
| 5,772,636 | 6/1998 | Brimhall et al. | 604/198 |
| 5,792,122 | 8/1998 | Brimhall et al. | 604/263 |
| 6,004,294 | 12/1999 | Brimhall et al. | 604/164 |

FOREIGN PATENT DOCUMENTS

| 0 750 916 A2 | 1/1997 | (EP) . |
|---|---|---|
| WO 99/08742 | 2/1999 | (WO) . |

*Primary Examiner*—John D. Yasko
(74) *Attorney, Agent, or Firm*—Eric M. Lee, Esq.

(57) ABSTRACT

A catheter and introducer needle assembly with a compact needle shield is provide. The introducer needle includes an enlarged diameter portion. The needle shield is disposed inside the catheter hub. The needle shield includes a transverse barrier to prevent unwanted distal movement of the needle once the needle has been withdrawn into the needle shield. The needle shield also includes a small diameter proximal opening to limit proximal movement of the needle out of the needle shield.

3 Claims, 10 Drawing Sheets

COMPACT NEEDLE POINT SHIELD

BACKGROUND OF THE INVENTION

The subject invention relates to a catheter and introducer needle assembly that includes a needle shield that will safely shield the sharp distal tip of the introducer needle after the needle has been used to insert the catheter into a patient.

Catheters, particularly intravascular (IV) catheters, are used for infusing fluid, such as normal saline solution, various medicaments and total parenteral nutrition, into a patient or withdrawing blood from a patient. Peripheral IV catheters tend to be relatively short, and are on the order of about one and one-half inches in length. The most common type of IV catheter is an over the needle peripheral IV catheter. As its name implies, an over the needle catheter is mounted over an introducer needle having a sharp distal tip. The catheter and the introducer needle are assembled so that the distal tip of the introducer needle extends beyond the distal tip of the catheter with the bevel of the needle facing up away from the patient's skin.

The catheter and introducer needle assembly is inserted at a shallow angle through the patient's skin into a peripheral blood vessel, i.e a smaller blood vessel that is not connected directly to the heart but is one of the branches of the central blood vessels that is directly connected to the heart. In order to verify proper placement of the assembly in the blood vessel, the clinician confirms that there is flashback of blood in the needle and in a flashback chamber located at the proximal end of the needle, which is typically formed as part of the needle hub. Once proper placement is confirmed, the clinician applies pressure to the blood vessel by pressing down on the patient's skin over the distal tip of the introducer needle and the catheter. This finger pressure occludes further blood flow through the introducer needle. The clinician withdraws the introducer needle, leaving the catheter in place, and attaches a fluid handling device to the catheter hub. Once the introducer needle is withdrawn from the catheter, it is a "blood contaminated sharp" and must be properly handled.

In recent years, there has been great concern over the contamination of clinicians with a patient's blood and a recognition that "blood contaminated sharps" must be immediately disposed. This concern has arisen because of the advent of currently incurable and fatal diseases, such as Acquired Immunosuppressive Deficiency Syndrome ("AIDS"), which can be transmitted by the exchange of body fluids from an infected person to another person. Thus, contact with the body fluid of an AIDS infected person must be avoided. As noted above, if an introducer needle has been used to place a catheter in the vein of an AIDS infected person, the introducer needle is a vehicle for the transmission of the disease. Although clinicians are aware of the need to properly handle "blood contaminated sharps", unfortunately in certain medical environments, such as emergency situations or as a result of inattention or neglect, needlesticks with contaminated introducer needles still occur.

As a result of the problem of accidental needlesticks by "blood contaminated sharps", various needle shields have been developed. Generally, such needle shields work for their intended purpose but could be improved. For example, some needle shields are bulky, difficult to use or require special features or techniques to be operative.

SUMMARY OF THE INVENTION

It is therefore an object of this invention to provide a needle shield that is compact.

It is another object of this invention to provide a needle shield that is simple and easy to use.

It is still another object of this invention to provide a needle shield that requires no special features or technique to be operative.

The catheter and introducer needle assembly with needle shield of this invention includes a catheter having a distal end and a proximal end connected to the distal end of a catheter hub. The introducer needle has a sharp distal tip and a proximal end connected to the distal end of a needle hub. A flashback chamber is defined in the needle hub. Typically a vented plug is located in the open proximal end of the flashback chamber to allow air to escape from the flashback chamber when blood enters the flashback chamber from the introducer needle. The catheter is coaxially disposed over the introducer needle so the sharp distal tip of the introducer needle is distal of the distal end of the catheter. The introducer needle also defines, along a distal portion thereof, an enlarged diameter portion.

The needle shield includes a main body portion defining a main chamber into which the introducer needle extends, a proximal opening and a distal opening. The proximal opening has a diameter sufficient to allow the proximal portion of the introducer needle to extend therethrough but that is too small to allow the enlarged diameter portion of the introducer needle to pass therethrough. Thus, the enlarged diameter portion of the needle in cooperation with the size of the proximal opening prevents unwanted proximal movement of the introducer needle with respect to the needle shield once the introducer needle has been withdrawn into the needle shield after use. Alternatively, a separate telescoping element may be disposed in the needle shield to cooperate with the enlarged diameter portion of the introducer needle to prevent unwanted proximal movement of the introducer needle. A movable transverse barrier adjacent to the distal opening to the needle shield flexes out of the way to allow the introducer needle to be withdrawn proximally into the main chamber. Once the sharp distal tip of the needle has been withdrawn proximal of the distal opening, the transverse barrier returns to its unbiased position covering the distal opening to prevent unwanted distal movement of the introducer needle and to capture the sharp distal tip of the needle in the main chamber.

The needle shield is sized so that it fits snugly within the catheter hub. There should be an interference fit between the outside of the needle shield and the inside of the catheter hub so that the needle shield cannot be easily removed from the catheter hub. Conversely, the interference fit should not be so tight as to cause difficulty in removing the needle shield from the catheter hub when desired.

BRIEF DESCRIPTION OF THE DRAWINGS

The preferred embodiments are illustrated in the drawings in which like reference numerals refer to like elements and in which.

DETAILED DESCRIPTION OF THE INVENTION

As used herein, the term "proximal" refers to a location on the catheter and introducer needle assembly with the compact needle shield of this invention closest to the clinician using the device and farthest from the patient in connection with whom the device is used when the device is used in its normal operation. Conversely, the term "distal" refers to a location on the catheter and introducer needle assembly with the compact needle shield of this invention farthest from the clinician using the device and closest to the patient in connection with whom the device is used when the device is used in its normal operation.

The catheter and introducer needle assembly with the compact needle shield of this invention is identified generally by the numeral 10. It includes a catheter assembly 20 and an introducer needle assembly 30 that includes a needle shield 40.

Catheter assembly 20 includes a catheter 21 that has a proximal end, a distal end and a catheter hub 24 affixed to the proximal end of catheter 21. Suitable materials for catheter 21 include, but are not limited to, thermoplastic resins such as polytetrafluoroethylene (PTFE), fluorinated ethylene propylene copolymer (FEP), polyurethane and the like. Preferably, catheter 21 is formed from a thermoplastic hydrophilic polyurethane that softens with exposure to physiological conditions present in the patient's body. Suitable materials for catheter hub 24 include, but are not limited to, thermoplastic polymeric resins such as polycarbonate, polystyrene, polypropylene and the like. Catheter hub 24 may include a radially outwardly extending tab, not shown, which is useful for advancing catheter 21 into the patient's blood vessel.

Introducer needle assembly 30 includes introducer needle 31 having a sharp distal tip defined by bevel 32 and a proximal end connected to needle hub 34. Introducer needle 31 is preferably formed from stainless steel. Needle hub 34 can include an integrated flashback chamber having an open proximal end. Needle hub 34 is preferably formed from the same types of materials that are used to form catheter hub 24. Preferably, the open proximal end of needle hub 34 is closed to fluid flow by a vented plug 36 which allows air but not liquid, such as blood, to flow therethrough.

Introducer needle assembly 30 also includes needle shield 40 which includes main body portion 41 and which in turn defines a main chamber 42 having a proximal opening 43. A cap 47 covers the distal end of main chamber 42 and defines a distal opening 44 therein. This allows introducer needle 31 to extend longitudinally through main body portion 41. The diameter of proximal opening 43 is slightly larger than the diameter of the main portion of introducer needle 31. This allows the main portion of introducer needle 31 to easily pass through proximal opening 43. Main body portion 41 also includes a flexible transverse barrier 46 which is held in place over the distal end of main chamber 42 by cap 47 so as to occlude distal opening 44. Transverse barrier 46 allows the sharp distal tip of introducer needle 31 to be withdrawn into needle shield 40 but thereafter prevents reexposure of the sharp distal tip through distal opening 44.

Needle shield 40 is sized so that it fits snugly within catheter hub 24. There should be enough interference between the outside of needle shield 40 and the inside of catheter hub 24 so that needle shield 40 cannot be easily removed from catheter hub 24. Conversely, the interference should not be so great as to cause difficulty in removing needle shield 40 from catheter hub 24 when desired. One mechanism for achieving this is to include ribs (not shown) formed on the inner surface of catheter hub 24 or the outer surface of needle shield 40. These ribs could be cantilevered if desired. Preferably the ribs create an interference between needle shield 40 and catheter hub 24 so the ribs would be deformed or bent out of the way when needle shield 40 is placed inside catheter hub 24.

Figure 1:
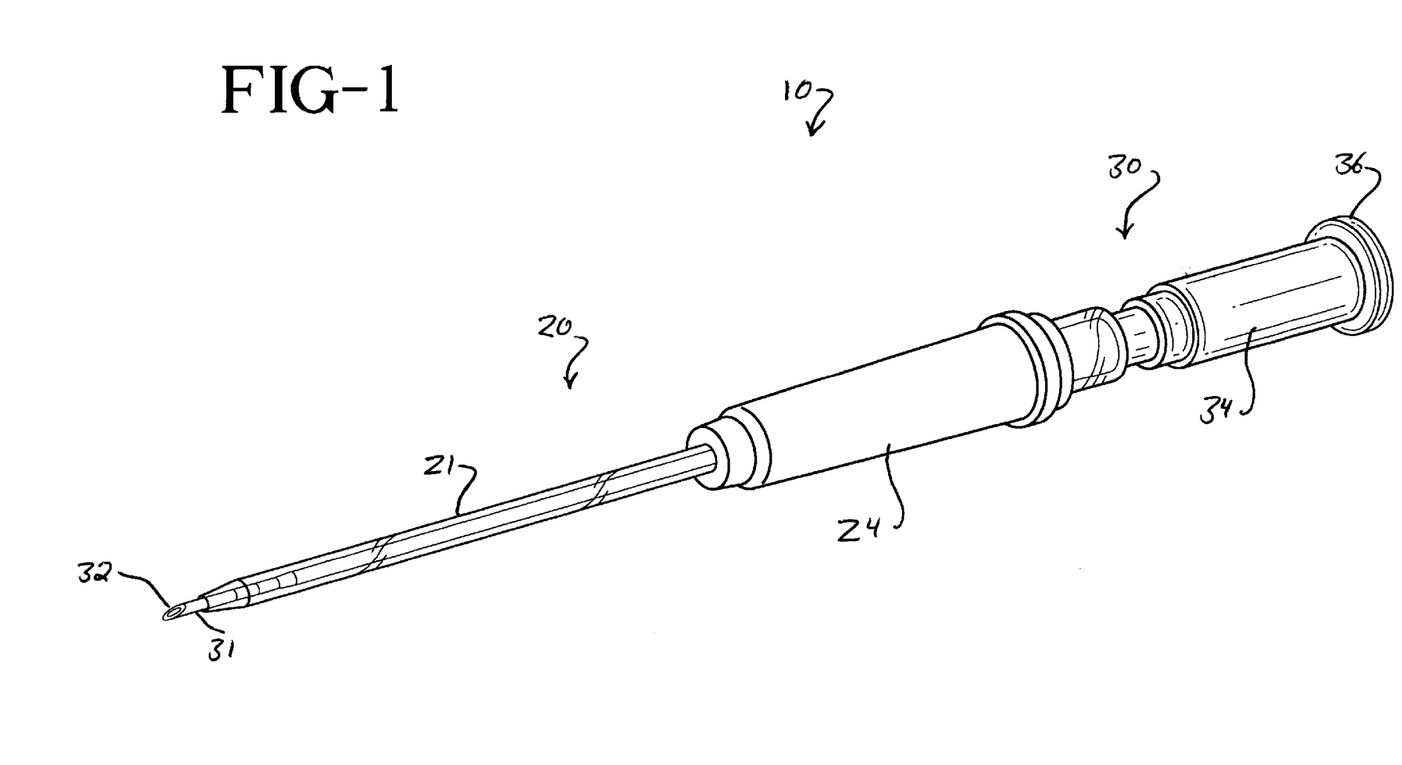
FIG. 1 is a perspective view of the catheter and introducer needle assembly with the compact needle shield of this invention.
Figure 2:
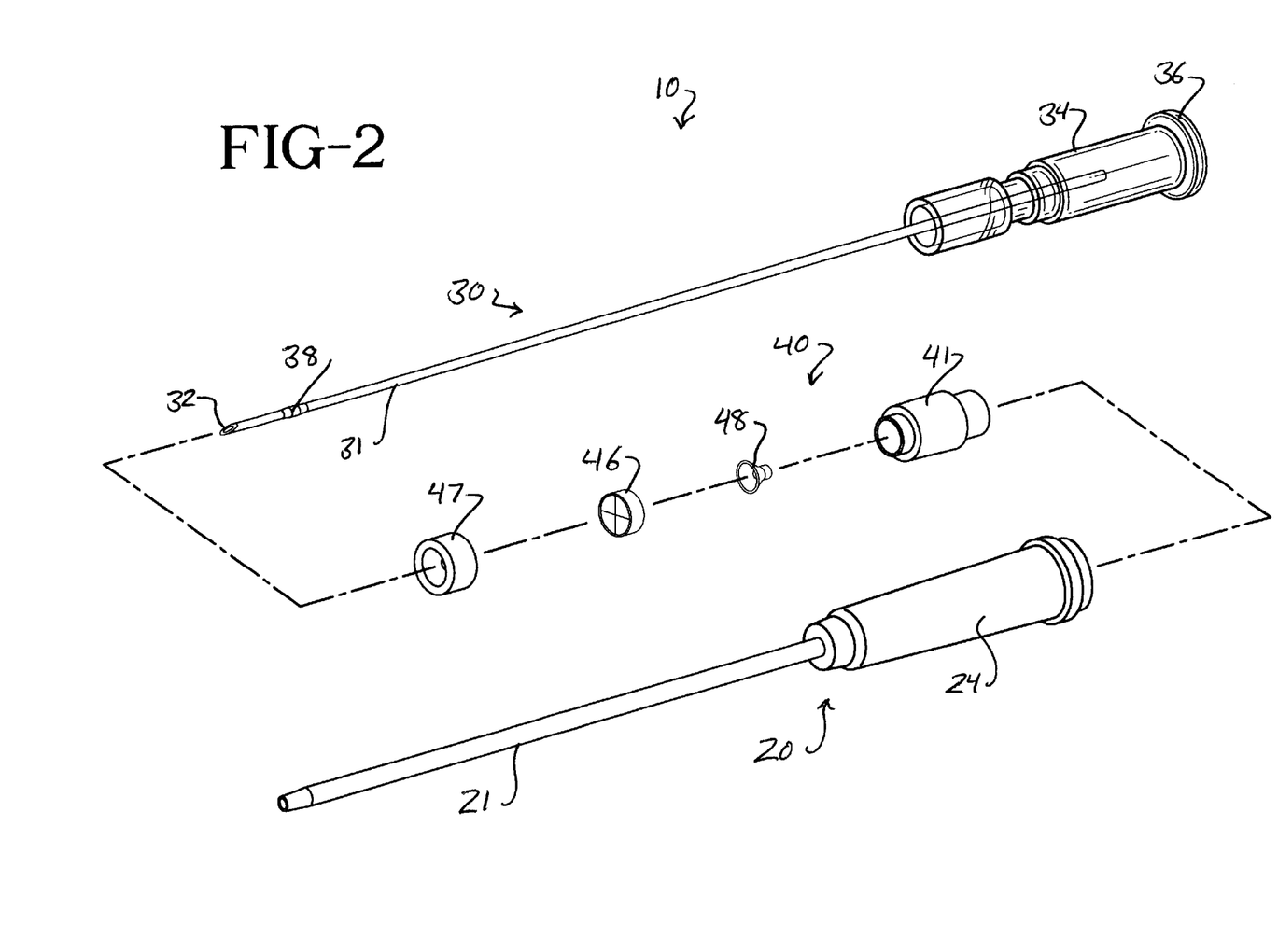
FIG. 2 is an exploded perspective view of the catheter and introducer needle assembly with the compact needle shield of this invention.
Figure 3:
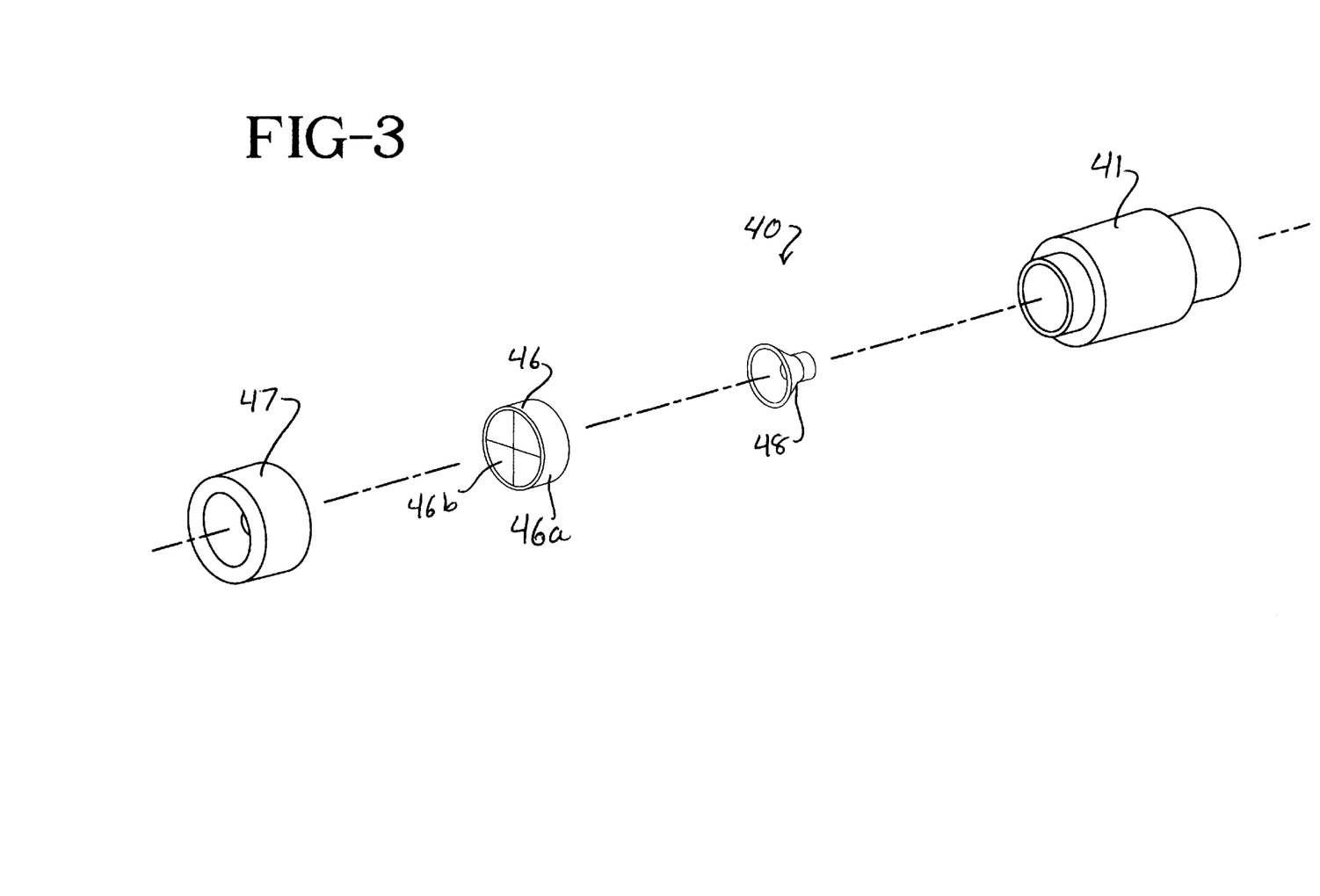
FIG. 3 is an exploded perspective view of the compact needle shield of this invention.

Introducer needle 31 includes an enlarged diameter portion 38. See FIG. 2. Enlarged diameter portion 38 can be formed on introducer needle 31 by forming a crimp on introducer needle 31. Alternatively, enlarged diameter portion 38 may be formed on introducer needle 31 by centerless grinding a larger diameter introducer needle.

Figure 9:
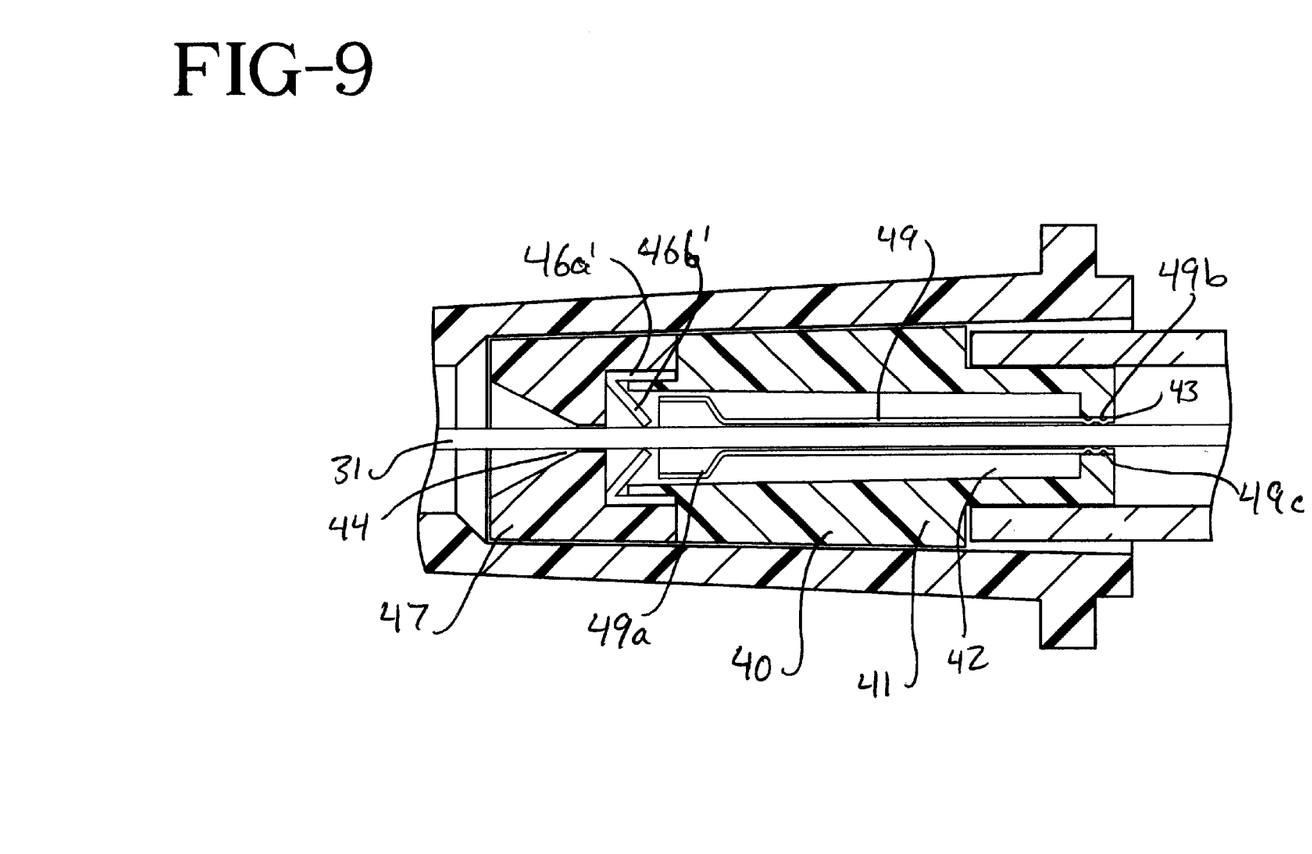
FIG. 9 is an enlarged cross-sectional view similar to FIG. 5 but of a second embodiment of the compact needle shield.
Figure 10:
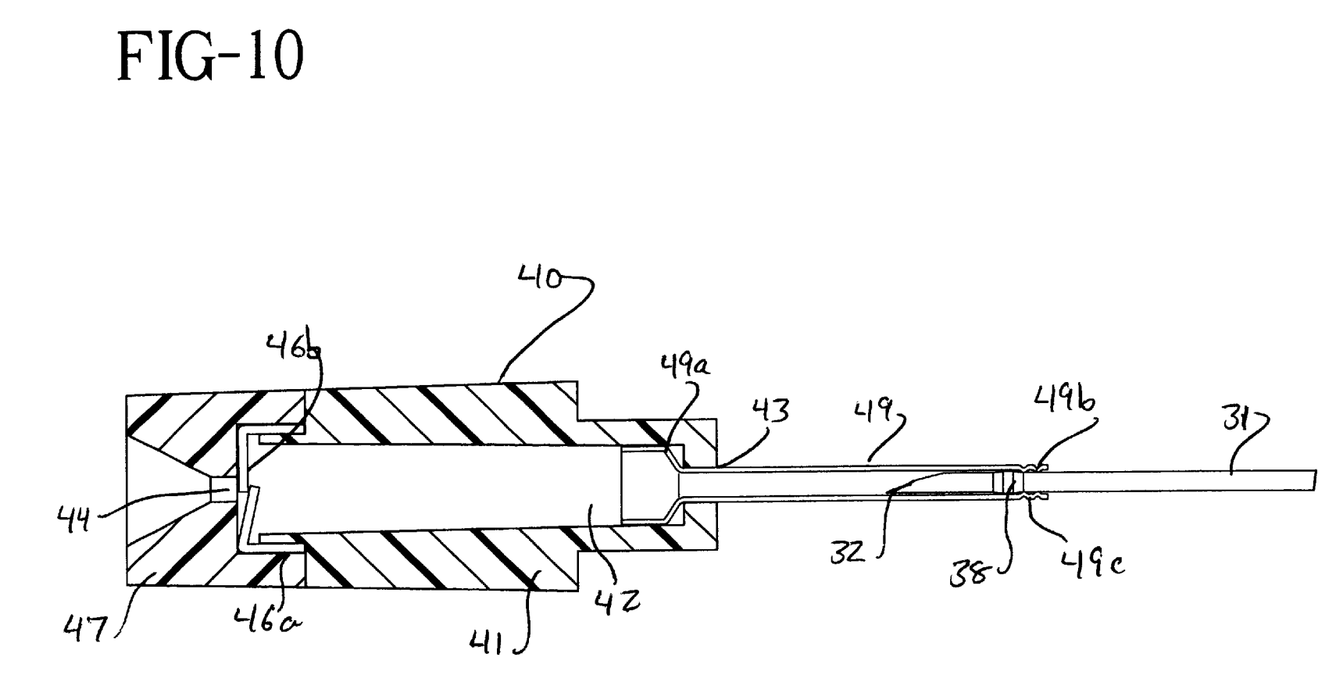
FIG. 10 is an enlarged cross-sectional view of the second embodiment of the compact needle shield removed from the catheter hub with the sharp distal tip of the introducer needle locked in the compact needle shield.

Enlarged diameter portion 38 should have a diameter greater than the diameter of proximal opening 43. This ensures that introducer needle 31 cannot be pulled in a proximal direction completely out of needle shield 40 because enlarged diameter portion 38 blocks further movement of introducer needle 31 through proximal opening 43. Alternatively and preferably, a metallic washer 48 having an opening therein with a diameter smaller than the diameter of enlarged diameter portion 38 can be placed over proximal opening 43 to prevent enlarged diameter portion 38 from passing into proximal opening 43. Another alternative is to use a telescoping member 49 having an enlarged distal portion 49a and a reduced diameter portion 49b. See FIGS. 9 and 10. Such a telescoping feature provides a device that is compact prior to use. Enlarged distal portion 49a engages proximal opening 43 to prevent telescoping member 49 from being pulled proximally completely out of needle shield 40. Reduced diameter portion 49b engages enlarged diameter portion 38 to prevent introducer needle 31 from being pulled proximally completely out of needle shield 40. Reduced diameter portion 49b may have a crimped portion 49c to minimize drag on introducer needle 31 while still ensuring that reduced diameter portion 49b prevents enlarged diameter portion 38 from passing therethrough.

Transverse barrier 46 is formed from a resilient material, preferably a stainless steel shim, and includes a mounting ring 46a securely mounted to needle shield 40 cap 47 which is bonded to main body 41. Transverse barrier 46 also includes a plurality of shielding flaps 46b that are formed to be generally perpendicular to mounting ring 46a so they cover distal opening 44 when in their normal rest position.

Figure 4:
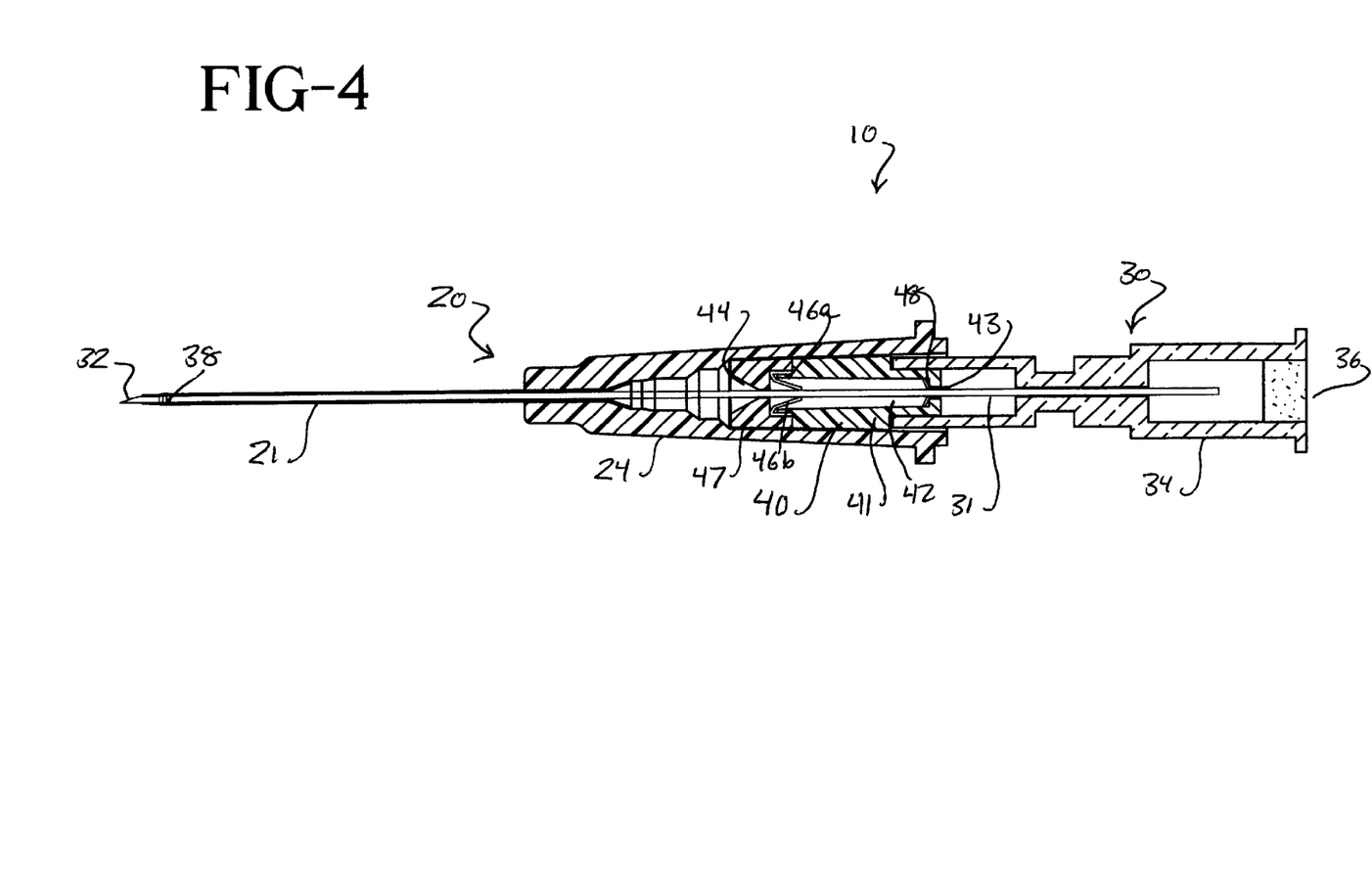
FIG. 4 is a cross-sectional view of one embodiment of the catheter and introducer needle assembly with the compact needle shield of this invention.
Figure 5:
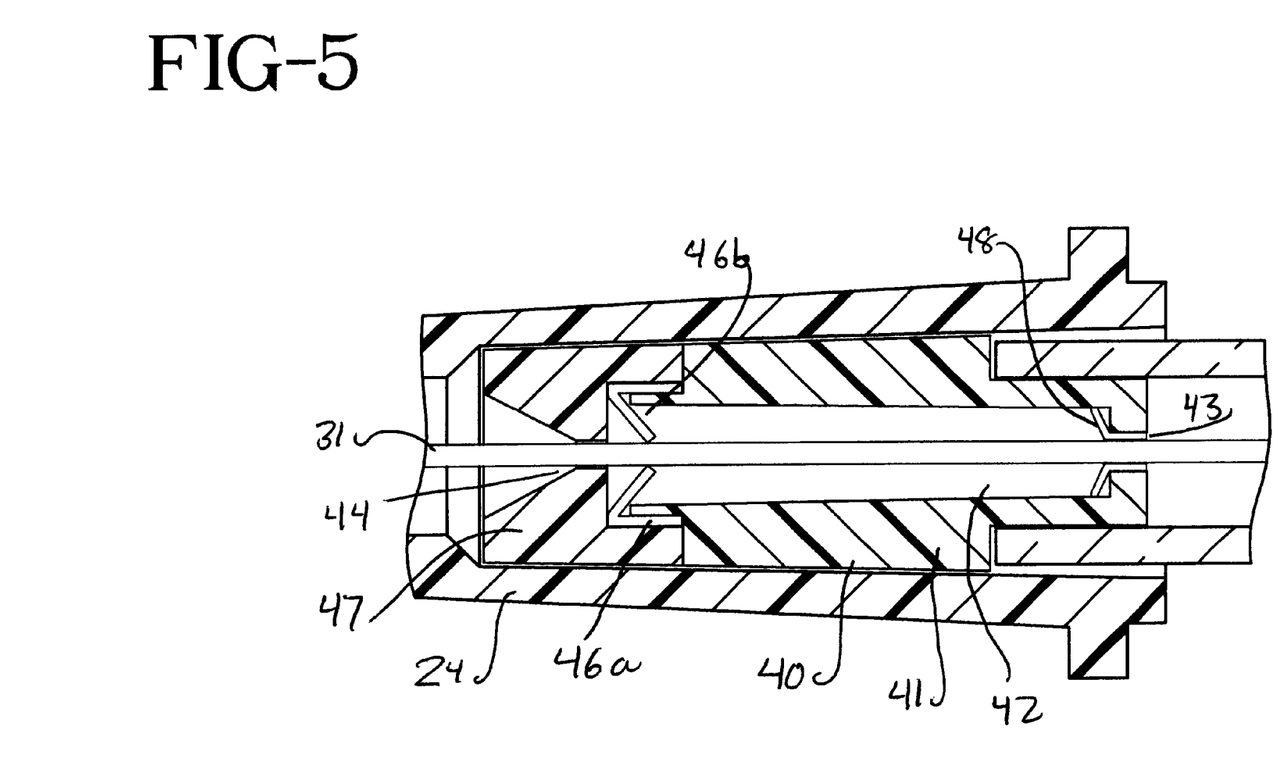
FIG. 5 is an enlarged cross-sectional view of one embodiment of the compact needle shield disposed in the catheter hub with the the sharp distal tip of the introducer needle distal of the compact needle shield.
Figure 6:
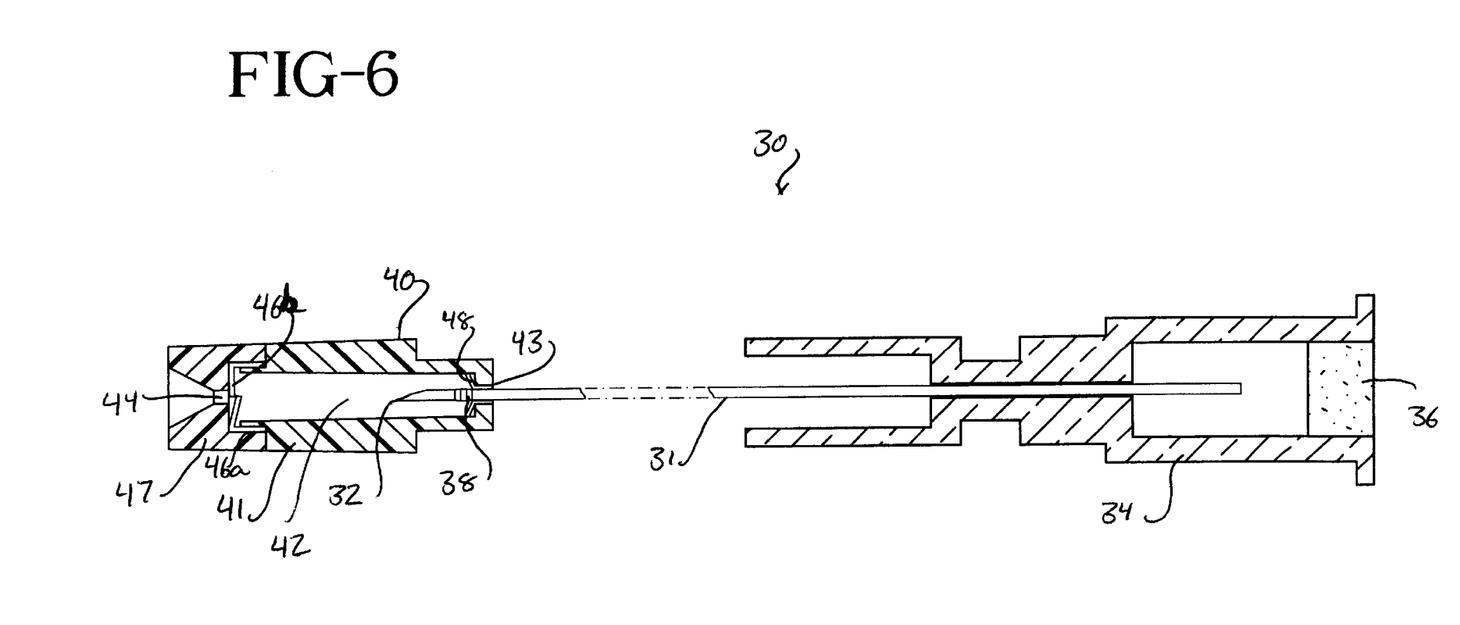
FIG. 6 is a cross-sectional view of one embodiment of the compact needle shield removed from the catheter hub with the sharp distal tip of the introducer needle locked in the compact needle shield.
Figure 7:
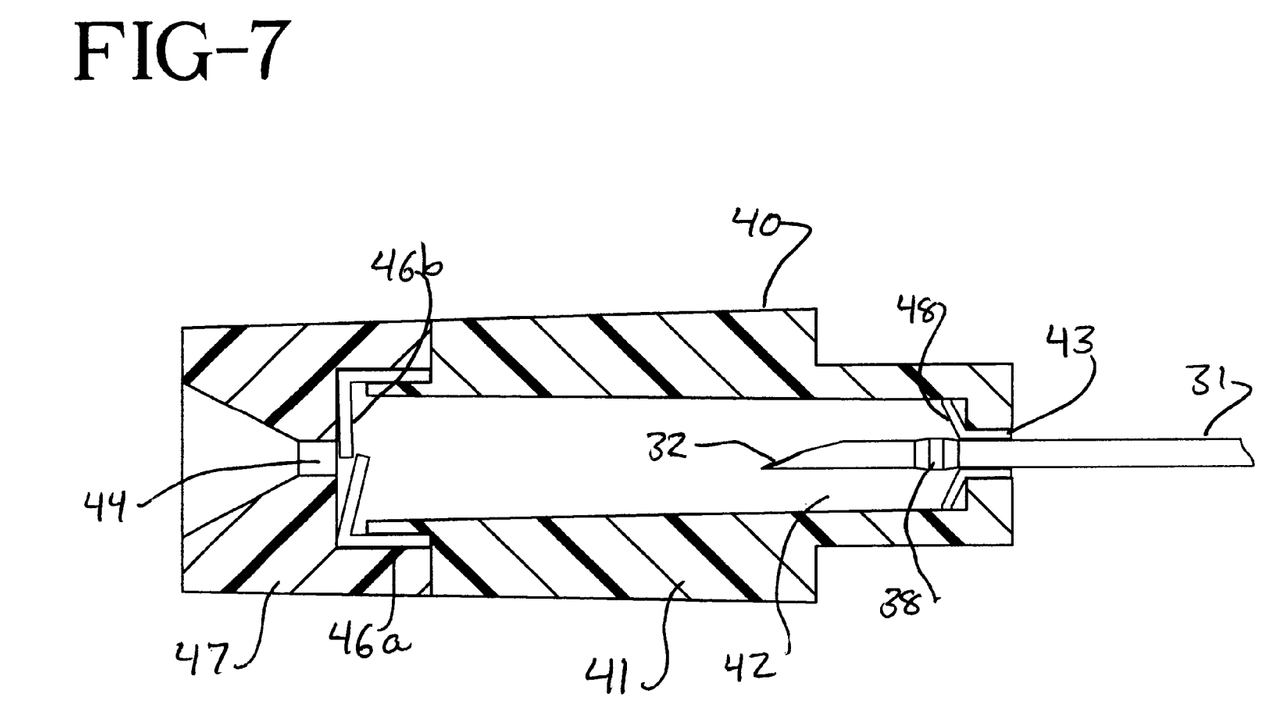
FIG. 7 is an enlarged cross-sectional view of one embodiment of the compact needle shield with the sharp distal tip of the introducer needle locked in the compact needle shield.
Figure 8:
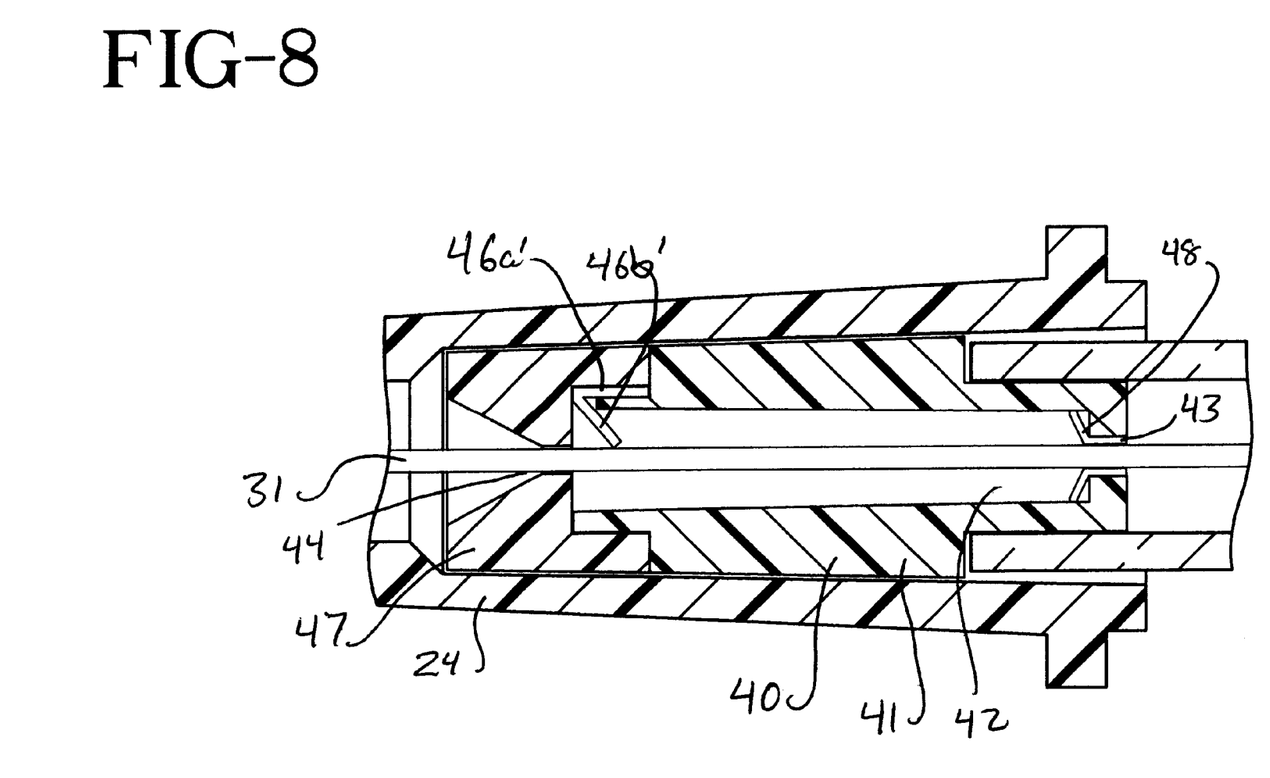
FIG. 8 is an enlarged cross-sectional view similar to FIG. 5 but with a different transverse barrier disposed in the compact needle shield.

When sharp distal tip 32 of introducer needle 31 is distal of distal opening 44, shielding flaps 46b are biased away from its normal position by introducer needle 31. See FIGS. 4 and 5. When introducer needle 31 is withdrawn proximally so the sharp distal tip 32 is proximal of distal opening 44, shielding flaps 46b will no longer abut the shaft of introducer needle 31 and can return to their normal position covering distal opening 44. See FIGS. 6 and 7. In this manner, sharp distal tip 32 is prevented from being reexposed through distal opening 44 by transverse barrier 46. A variation of transverse barrier 46 can be seen in FIG. 8 where a single mounting leg 46a' and a single shielding flap 46b' are used.

In order to place catheter 21 into a patient's blood vessel, the clinician substantially longitudinally aligns introducer needle 31 and catheter 21 with the target blood vessel. Bevel 32a should be facing substantially away from the skin surface during venipuncture. The clinician inserts introducer needle 31 and catheter 21 at a shallow angle, preferably less than about 35 degrees, into the skin so that the sharp distal tip enters the target blood vessel. The clinician then preferably observes a blood flashback in the flashback chamber of needle hub 34.

After confirming placement of introducer needle 31 and catheter 21 in the target blood vessel, the clinician advances catheter 21 distally axially along introducer needle 31 into position in the blood vessel. After proper placement of catheter 31 is achieved, the clinician places a finger from her other hand on the patient's skin over the blood vessel approximately over the distal end of catheter 31. By placing her finger on the patient's skin and applying sufficient pressure on the skin, the clincan thereby substantially occludes blood flow through catheter 31. The clinican then withdraws introducer needle 31 from catheter 21 by moving needle hub 34 proximally. This movement causes introducer needle 31 to move proximally into needle shield 40. However, the interference fit between needle shield 40 and catheter hub 24 cause needle shield 40 to remain engaged with catheter hub 24 during at least the initial proximal movement of introducer needle 31. Continued proximally directed force applied to needle hub 34 overcomes the resistive force of the interference fit and allows needle shield 40 to become disengaged from catheter hub 21 once the sharp distal tip is located in needle shield 40 and introducer needle 31 is locked therein. After introducer needle 31 and needle shield 40 have been removed from catheter hub 21, the clinician may then attach any desired fluid handling device to catheter hub 21 and commence the planned treatment. Introducer needle 31 and needle shield 40 may then be disposed of according to the facility's disposal protocol.

Thus, it is seen that a catheter and introducer needle assembly with needle shield is provided that is compact, simple and easy to use and that requires no special features or technique to be operative.

I claim:

1. A catheter and introducer needle assembly, comprising:

a catheter having a proximal end and distal end;

a catheter hub in fluid communication with the catheter and having a proximal end and a distal end connected to the proximal end of the catheter;

an introducer needle disposed in the catheter and having a proximal end and a distal end and defining an enlarged diameter portion; and a needle shield having a proximal end and a distal end disposed within the catheter hub with an interference fit, the needle shield defining a main chamber in the catheter hub with the introducer needle extending through the chamber wherein the needle shield has a means for engaging the enlarged diameter portion of the introducer needle to prevent unwanted proximal movement of the introducer needle and wherein the needle shield includes a means for engaging the introducer needle to prevent unwanted distal movement of the introducer needle wherein the means is a resilient transverse barrier defining a plurality of shielding flaps disposed in the chamber.

2. A catheter and introducer needle assembly, comprising:

a catheter having a proximal end and distal end;

a catheter hub in fluid communication with the catheter and having a proximal end and a distal end connected to the proximal end of the catheter;

an introducer needle disposed in the catheter and having a proximal end and a distal end and defining an enlarged diameter portion;

a needle shield having a proximal end and a distal end disposed within the catheter hub with an interference fit, the needle shield defining a main chamber that is located in the catheter hub with the introducer needle extending through the chamber wherein the needle shield has a proximal opening that has a diameter smaller than the diameter of the enlarged diameter portion of the introducer needle and wherein the needle shield includes a resilient transverse barrier defining a plurality of shielding flaps disposed in the chamber adjacent to a distal opening in the needle shield; and a telescoping member having a proximal end and a distal end slidably disposed in the needle shield through the proximal opening wherein the telescoping member has an enlarged diameter portion adjacent to the distal end and a reduced diameter portion adjacent to the proximal end.

3. The catheter and introducer needle assembly of claim 2 wherein the reduced diameter portion is crimped.

* * * * *